United States Patent
Moens

[11] Patent Number: 5,919,927
[45] Date of Patent: Jul. 6, 1999

[54] PURIFICATION OF CAPROLACTAM FROM RECYCLED NYLON

[75] Inventor: Luc Moens, Lakewood, Colo.

[73] Assignee: Midwest Research Institute, Kansas City, Mo.

[21] Appl. No.: 09/058,403

[22] Filed: Apr. 9, 1998

[51] Int. Cl.$^6$ .................................................. C07D 201/16
[52] U.S. Cl. ........................ 540/540; 540/485; 564/502
[58] Field of Search .............................................. 540/540

[56] References Cited

U.S. PATENT DOCUMENTS

| 5,216,149 | 6/1993 | Evans et al. | 540/538 |
| 5,280,105 | 1/1994 | Moran, Jr. | 528/486 |
| 5,294,384 | 3/1994 | David et al. | 264/37 |

FOREIGN PATENT DOCUMENTS

| 4301406 | 7/1994 | Germany . | |

OTHER PUBLICATIONS

Puffr, R; Kubanek, V. Lactam–Based Polyamides, vol. 1 and 2; CRC Press Boca Raton, 1991.

*Primary Examiner*—John M. Ford
*Assistant Examiner*—Bruck Kifle
*Attorney, Agent, or Firm*—Ken Richardson

[57] ABSTRACT

A method of removing 1,11-diamino-6-undecanone from the pyrolysis product of nylon comprising:

a) pyrolyzing nylon-6 to form a pyrolyzate containing a caprolactam mixture;
b) dissolving the caprolactam mixture in a solvent to form a solution;
c) passing carbon dioxide gas through the solution to form a precipitate;
d) removing the precipitate from the solution; and
e) recovering the purified caprolactam from the solution.

18 Claims, 3 Drawing Sheets

ε-caprolactam →(Polymerization)→ NYLON-6

Problem:

Imine must be removed to avoid "gellation" of nylon-6 during polymerization

PURIFICATION OF CAPROLACTAM FROM RECYCLED NYLON

CONTRACTUAL ORIGIN OF THE INVENTION

The U.S. government has rights in this invention under Contract No. DE-AC36-83H10093 between the U.S. Department of Energy and Midwest Research Institute.

BACKGROUND OF THE INVENTION

I. Field of the Invention

In general, the invention relates to the field of obtaining purified materials from recycling, and more specifically, obtaining purified caprolactam from recycled nylon, as found in nylon carpeting.

The recycling nylon has been the focus of many years of research because of the simplicity of the concept and the attractiveness of potential economic benefits. The annual energy impact of this technology in the year 2010 is estimated to be approximately 23 trillion BTU for the expected production of 400 million pounds of $\epsilon$-caprolactam from waste carpet that is currently accumulating in landfills. This estimated energy consumption is based on the current production method for nylon-6 fiber from fossil resources.

In the recycling scheme, one processing step replaces nine processing steps in the production of $\epsilon$-caprolactam from crude oil. Thus, the 400 million pounds of $\epsilon$-caprolactam anticipated to be produced in 2010 can be produced from about 800 million pounds post-consumer carpet waste, while the non-nylon components of the carpet could be used to supply process energy.

II. The Prior Art

In the depolymerization of nylon-6 of waste carpet through pyrolysis to obtain $\epsilon$-caprolactam monomer for repolymerization into nylon, a significant obstacle is the formation of the undesirable by-product 1,11-diamino-6-undecanone in its amine form, referred to hereinafter as "imine".

In other words the caprolactam resulting from the depolymerization requires further purification before it can be effectively and efficiently repolymerized.

From Rudolph Puffr and Vladimir Kuba'nek, *Lactam-Based Polyamides*, Volume I and II; CRC Press, Inc.: Boca Raton, 1991, it was known that the main products of polyamide 6 burning (1000° C.) are $C_2$, caprolactam, and aromatic hydrocarbon; however, the possibility of the formation of hydrogen cyanide is acute during high temperature polyamide oxidation in a closed system when ammonia is formed from the —$NH_2$ end groups. Namely, when polyamide 6,11, 66 or 610 was oxided at 500° C. in the presence of $NH_3$ (0.5–5 g/100 g of polymer) considerable amounts of HCN were generated (2–4 g/100 g of polymer). Therefore, reliance on this process to provide caprolactam is fraught with the prospect of poisonous products such as HCN.

A process of using fast pyrolysis in a carrier gas to convert a polyamide containing a plastic waste feed stream comprising nylon 6 in a manner such that pyrolysis of the polyamide produces the high monomeric constituent caprolactam is disclosed in U.S. Pat. No. 5,216,149. However, the pyrolyzate of this process requires further purification to extract pure-crystalline caprolactam as the removal of impurities is crucial to the reusability of the caprolactam for production of nylon-6.

U.S. Pat. No. 5,280,105 discloses a method for separating nylon 6 polymer from a mixture thereof with nylon 6,6 polymer, comprising treating the mixture with an aqueous solution of an aliphatic carboxylic acid at a concentration and temperature sufficient at atmospheric pressure to dissolve nylon 6 polymer, while leaving nylon 6,6 and separating the solution of nylon 6 from the nylon 6,6 polymer. In other words, the separation of nylon 6 from nylon 6,6 is based on the differences in the solubilies of these nylon materials.

A process for forming a thermoplastic composition from carpet wherein a carpet sample is melt-blended without separating the carpet into its component parts is disclosed in U.S. Pat. No. 5,294,384. The carpet sample is preferrably a conventional sample of carpet comprising nylon tufts formed from nylon 6 or nylon 6,6 or blends or copolymers thereof, and at least one polyolefin backing material and a styrene-butadiene rubber (SBR) adhesive originally applied as a latex.

However, there is a need extant in the art of utilizing caprolactam from recycled nylon for repolymerization into nylon 6, to devise an efficient process for the selective removal of 1,11-diamino-6-undecanone from $\epsilon$-caprolactam generated through pyrolyis of nylon carpet. The process for selective removal of the 1,11 diamino-6-undecanone to effect purification of the final caprolactam containing pyrolyzate would constitute a critical step in developing this technology for commericalization for repolymerization of the caprolactam to nylon.

Recycling of nylon-6 containing carpet waste through pyrolysis technology leads to excellent yields of $\epsilon$-caprolactam, hereinafter referred to as caprolactam; however, purification of the final caprolactam containing pyrolyzate has proven to be very critical in developing this technology for commercialization.

SUMMARY OF THE INVENTION

One object of the present invention is to provide an efficient process for recovering caprolactam from recycled nylon containing materials.

Another object of the present invention is to provide an efficient process for recovering purified caprolactam from recycled nylon containing materials.

A further object of the present invention is to provide an efficient process for recovering caprolactam from recycled nylon containing materials by the selective removal of 1,11-diamino-6-undecanone from $\epsilon$-caprolactam generated through pyrolysis of recycled nylon containing materials.

A yet further object of the present invention is to provide an efficient process for recovering caprolactam from recycled nylon containing materials by removing the imine that would induce gellation of the nylon-6 during polymerization.

A further object yet still of the present invention is to provide an efficient process for recovering caprolactam from recycled nylon containing materials, by recovering caprolactam as a crystalline solid.

A still further object of the present invention is to provide an efficient process for recovering caprolactam from recycled nylon containing materials by removing the imine by the use of acetone and carbon dioxide.

In general, the invention is accomplished by:
  pyrolyzing a nylon-6 containing material to form a pyrolyzate containing a caprolactam mixture;
  dissolving the caprolactam mixture in a solvent to form a solution;
  passing carbon dioxide gas through the solution to form a precipitate;

removing the precipitate from the solution; and recovering the purified caprolactam from the solution.

BRIEF DESCRIPTION OF THE DRAWINGS

The accompanying drawings which are incorporated in and form a part of the specification will illustrate preferred embodiments of the present invention, and together with the description, will serve to explain the principles of the invention.

DETAILED DESCRIPTION OF THE INVENTION

Figure 1:
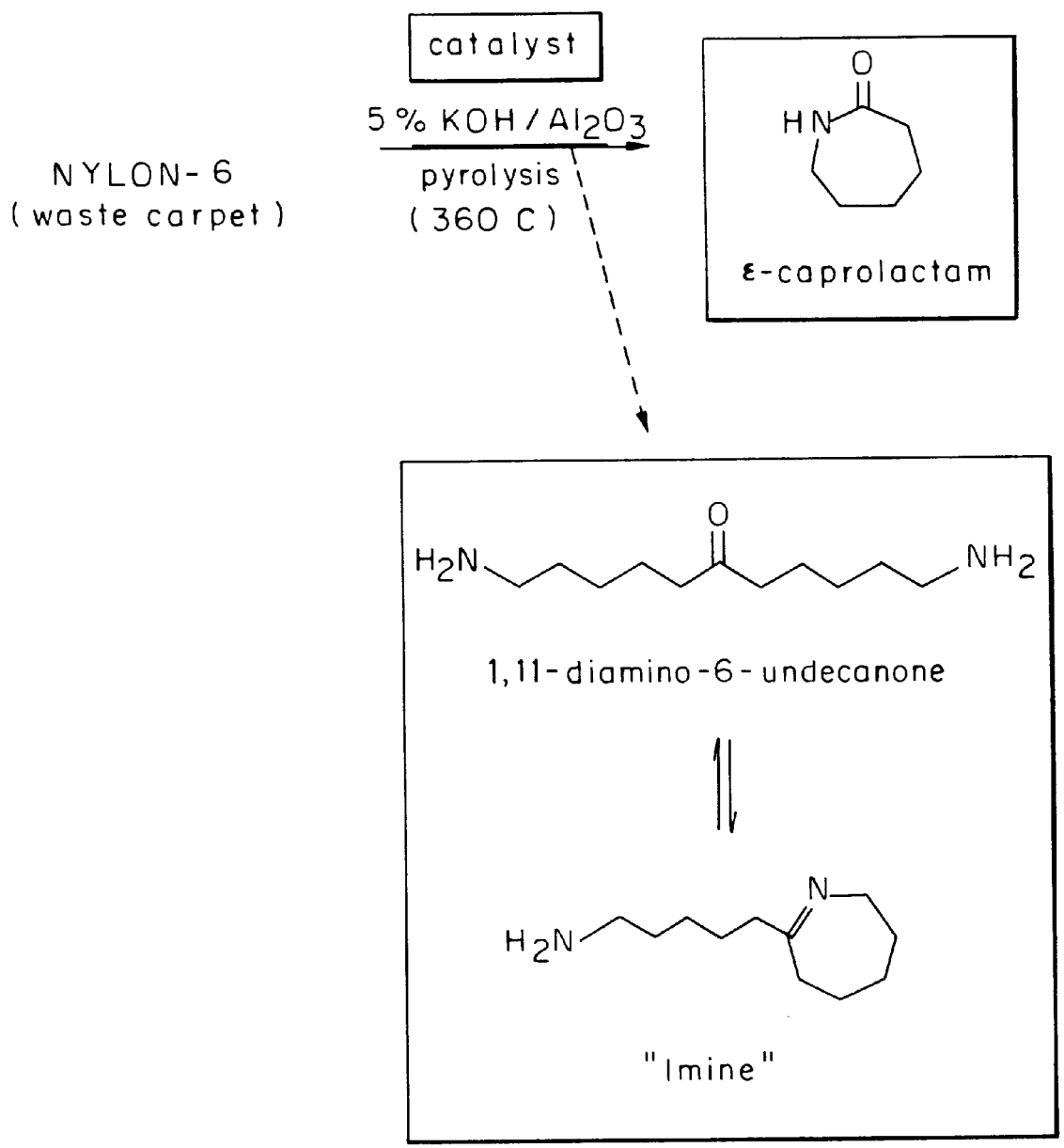
FIG. 1 is a flow chart detailing the depolymerization of nylon-6 through pyrolysis to produce ε-caprolactam along with 1,11-diamino-6-undecanone and its interchangable co-existent imine in equilibrium.

In general, the pyrolysis of nylon-6 waste carpet to obtain ε-caprolactam for purposes of repolymerizing the caprolactam to nylon-6 is encumbered by the undesirable by-product of 1,11-diamino-6-undecanone, which exists in equilibrium with its imine-form, as shown by FIG. 1.

The depolymerization of nylon-6 through pyrolysis generally proceeds at a temperature of about 360° C. in the presence of a catalyst of 5% $KOH/Al_2O_3$ as depicted in FIG. 1.

Figure 2:
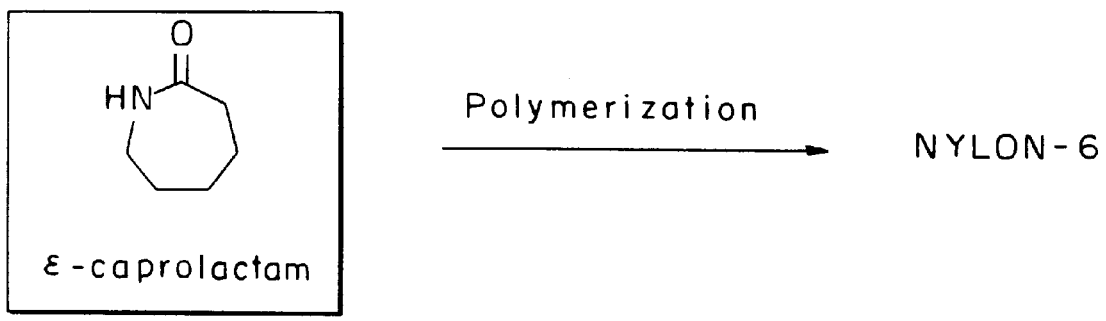
FIG. 2 is a schematic illustration of the re-polymerization of caprolactam to nylon-6 illustrating that, to avoid gellation of nylon-6 during polymerization, the problem of the presence of the imine, must be removed.
Figure 2:
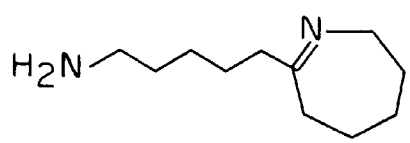

Once the ε-caprolactam is obtained through depolymerization by pyrolysis, the presence of the imine in association with the ε-caprolactam induces gellation of the nylon-6 during repolymerization of caprolactam to nylon-6, as depicted in FIG. 2. The representation of the equilibrium condition between the 1,11-diamino-6-undecanone and the imine obtained as a result of the depolymerization of a nylon-6 containing carpet is as follows:

the compound is free of solvent or when it is dissolved in aprotic solvents such as dichloromethane. Consequently, it should be recognized that this molecule has interchangeable structures depending on the medium in which it is dissolved. For purposes of this invention, the term "imine" is meant to include this molecule in any of its above-mentioned structures.

The presence of imine in the caprolactam in concentrations higher than 3 wt. % significantly inhibits repolymerization of the caprolactam. This inhibition is an economic obstacle to the efficient development of the recycle of nylon, especially as found in nylon carpet. This is evidenced by the lower molecular weight of nylon-6 that can be obtained after re-polymerization of the impure caprolactam.

While not intending to be bound by any particular theory, it is presumed that the regularity of the nylon-6 crystal structure is perturbed through cross-linking of the polyamide chains. This phenomenon is usually referred to as "gelling" or "gellation" and is described in Kamerbeek, B.; Kroes, G. H.; Grolle, W. *Soc. Chem. Ind. London, Monograph* 1961, 13, 357–391; and Stresinka, J.; Mokry, J. *Int. Polym. Sci. Technol.* 1974, 1, 98–103.

The result of this gellation is a low-grade caprolactam that has little value for fiber applications. It has been determined that the maximum allowable concentration of imine in the crude pyrolyzate should be 3% if inhibition of repolymerization of the caprolactam is to be avoided. Since this value is often exceeded in the crude caprolactam generated from nylon-6 pyrolysis, a simple, reliable and cost-effective purification method is needed. However, purification of caprolactam to acceptable limits of less than 3% imine has proven to be especially problematic due to the high polarity of both the caprolactam and the imine.

The present invention is able to attain acceptable limits of less than 3% by using inexpensive and environmentally acceptable materials such as carbon dioxide and acetone. German patent DE 43 01 406 A1-Nielinger, W. issued to Bayer AG in 1994, addressed the problem by heating the crude caprolactam with urea, followed by fractional distillation. The procedure apparently worked very well because no basic impurities (e. g. imine) could be detected in the purified caprolactam However, the use of urea followed by fractional distillation is not economically practical for the recycle of nylon from carpeting.

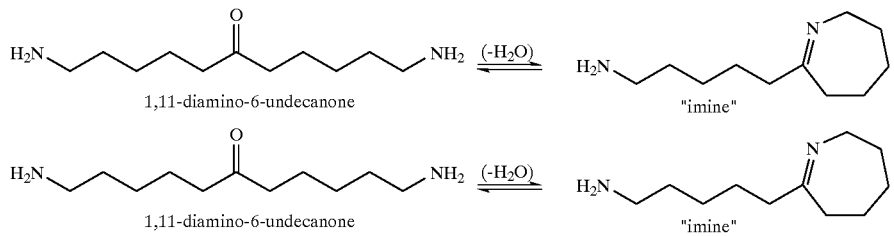

More specifically, the 1,11-diamino-6-undecanone spontaneously loses one molecule of water to form imine. This condensation reaction can be reversed when the imine is dissolved in an aqueous medium. It should be noted that the imine is obtained from the ketone through loss of one molecule of water. The imine is also known in the chemical literature under its full chemical name, as, 2-(5-aminopentyl)-4,5,6,7-tetrahydro-3H-azepine. This molecule is readily hydrolyzed to the open ketone form in an aqueous medium, while the imine form is the preferred form when The present invention offers a much simpler and more efficient process based on the specific immobilization of the imine as its "$CO_2$-adduct", which is believed to be a carbamate in the form of a white solid precipitate. The imine absorbs $CO_2$ from the air and forms a white solid capable of losing $CO_2$ reversibly, which regenerates the imine form when heated. The invention process incorporates a solvent that selectively dissolves the caprolactam while precipitating the carbamate. This simultaneous selective dissolution of the caprolactam and precipitation of the carbamate is achieved by dissolving the crude caprolactam in acetone or toluene and introducing a flow of $CO_2$ through the solution at ambient temperature while stirring. However, the invention process is operable at any temperature which permits the $CO_2$ to be solubilized in the solvent in order to facilitate reaction with the impurity. But, if the reaction temperature is too high, the $CO_2$ may not have sufficient solubility due to its high vapor pressure.

Figure 3:
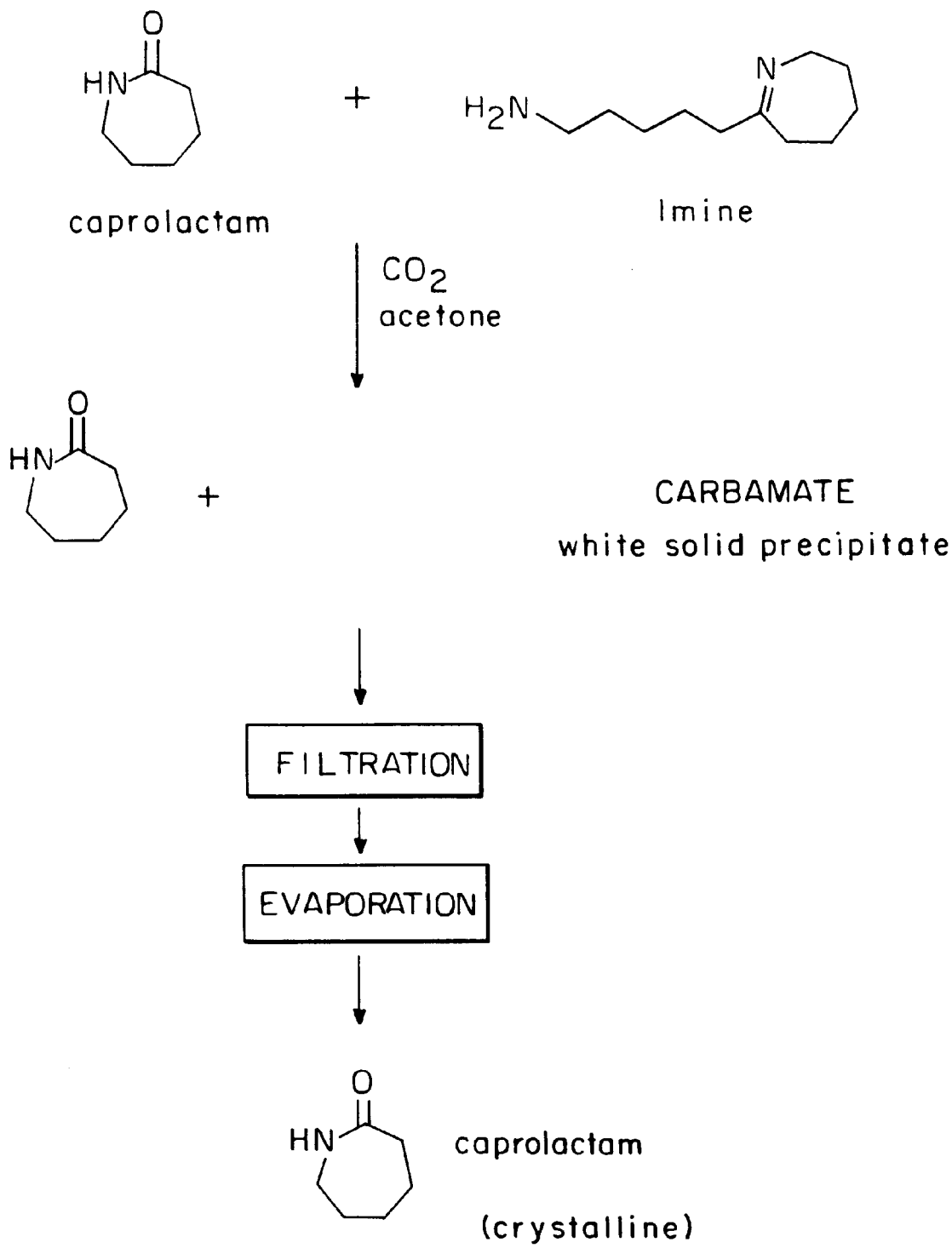
FIG. 3 is a schematic illustrating the process of the invention for obtaining ε-caprolactam in crystalline form from a mixture of ε-caprolactam and the imine resulting from the pyrolysis of recycled nylon containing materials.

The imine reacted immediately with the $CO_2$ to form the insoluble carbamate as a white precipitate as schematically depicted in FIG. 3.

The fine white solid is filtered off and the filtrate, which consists of caprolactam, is concentrated.

While the following examples will illustrate specific methods for carrying out the present invention, it is to be understood that the invention is not limited to these specific embodiments, as various modifications of the described modes for carrying out the invention can be performed by those skilled in the art of nylon recycling or related fields without departing from the spirit and scope of the present invention.

Table I shows experimental data on a mixture of pure caprolactam with 10% pure imine (first entry), as well as on Runs 3.3 and 3.5 (which refers to pyrolysis runs for the production of pyrolyzate from nylon-6 carpet waste fluff, described in Examples 8 and 9, respectively).

difficult drying step under high vacuum and is therefore not practical. It can be seen that the purification is very efficient in removing most of the imine when Celite® is used. Although Celite® from Aldrich Chemical Company from Milwaukee, Wis., was used, it is contemplated that any silica filter system such as diatomacous earth could be used.

Even though the resulting caprolactam is still yellow in color, GC-MS analysis has shown that 0% concentration of imine can be achieved if the fine carbamate is filtered off efficiently through a pad of silica gel. The GC-MS used was a Hewlett-Packard (Wilmington, Del.) model number 5890 Gas Chromatograph coupled to a 5970 Mass Selective Detector. Another advantage of this method of the invention is that upon dissolution of the crude caprolactam in acetone, a brown precipitate forms which consists of cyclic oligomers of nylon-6.

Table II illustrates several replicate experiments on crude caprolactam of Run 3.3 using $CO_2$ method with the only difference being the scale of the reaction (10–40 g).

TABLE I

Experiments for the removal of imine from the crude ε-caprolactam

| CPL | concentration of imine | solvent | isolated CPL | conc. isolated imine | comments |
| --- | --- | --- | --- | --- | --- |
| 8.57 g | 10% | water | 8.89 g | 1.73 ± 0.08% | requires evaporation of $H_2O$ |
| (Run 3.3) 8.34 | 1.5% | water | 6.68 g | 0.24 ± 0.29% | filtration through Celite ® |
| (Run 3.5) 8.10 g | 3% | water | — | 0.22 ± 0.02% | filtration through Celite ® |
| (Run 3.5) 7.73 g | 3% | toluene | 6.46 g | 1.05 ± 0.07% | filtration through Celite ® |
| (Run 3.5) 7.08 g | 3% | acetone | 6.61 g | 1.06 ± 0.15% | filtration through Celite ® |
| (Run 3.5) 7.16 g | 3% | acetone | 7.0 g | 0.92 ± 0.00% | filtration through Celite ® |
| (Run 3.5) 7.26 g | 3% | acetone | 6.55 g | 0.00 ± 0.00% | filtration through silica gel |

The solvents used in the purification experiments were water, toluene and acetone. The use of water required a

TABLE II

| CRUDE CPL (g) | RECOVERED CPL (g) | RECOVERED CPL (%) | conc. of imine (%) | ISOLATED IMPURITIES (wt %) | TOTAL MASS RECOVERY (*) (%) |
| --- | --- | --- | --- | --- | --- |
| 10.38 | 9.095 | 88 | 0.00 ± 0.00 | 5.6 | 93.3 |
| 10.942 | 9.753 | 89 | 0.00 ± 0.00 | 12.9 | 102 |
| 40.63 | 36.15 | 89 | 0.00 ± 0.00 | 16.9 | 106 |
| 13.584 | 11.700 | 86.1 | 0.00 ± 0.00 | 37.4 | 123 |

TABLE II-continued

| CRUDE CPL (g) | RECOVERED CPL (g) | RECOVERED CPL (%) | conc. of imine (%) | ISOLATED IMPURITIES (wt %) | TOTAL MASS RECOVERY (*) (%) |
|---|---|---|---|---|---|
| 21.005 | 17.498 | 83.3 | 0.00 ± 0.00 | 13.8 | 97 |
| 11.230 | 9.860 | 88 | 0.00 ± 0.00 | 14.4 | 102 |

Replicate experiments for the purification of crude ε-caprolactum produced Run 3.3.
(Analysis of crude pyrolyzate before purification: 84% caprolactam CPL; 1.7% imine; 14.3% unknown)
(*) uncorrected for possible residual solvent.

Again, the imine is completely removed from the crude caprolactam. The recovered caprolactam indicated here reflects high purity as determined by GC-analysis. The weight of isolated impurities that comprises the imine-derivative and the cyclic oligomers is misleading since no attempts were made to ensure that all solvent was removed from this fraction. This is reflected in the total mass recovery greater than 100%.

The brown precipitate that comprises the impurities other than the imine, may also contain decomposition products originating from the backing material of the initial nylon carpet. The purified caprolactam is yellow-brown in color, but apart from being imine-free, its NMR spectrum looks very good compared to the spectrum of a commercial caprolactam sample.

A further advantage of the present invention process is that the acetone may be recycled in this process.

EXAMPLE 1

A mixture of imine (930 mg) (synthesized according to Kamerbeek, supra) and commercially pure caprolactam (8.57 g) (Aldrich Chem. Co., Milwaukee, Wis.) were dissolved in 9 mL water and $CO_2$ generated from dry ice was bubbled through the solution for 7 hours. The water was then removed using a rotary evaporator (water bath max. 35° C.) followed by complete drying under high vacuum. The solid was then dissolved in 50 mL acetone and the solution was stirred at room temperature for 2.5 hours. The fine, suspended solid was filtered off and the clear filtrate was concentrated in vacuo to give 8.887 g of white caprolactam. This sample was then molten in order to decompose any residual carbamate to imine. The resulting material was analyzed by gas chromatography and was found to contain 94.69% caprolactam (±2.11) and 1.73% imine (±0.08).

EXAMPLE 2

Caprolactam-containing pyrolyzate generated in a fluidized bed reactor

A sample of 8.34 g caprolactam-containing pyrolyzate generated in Run 3.3 (nylon-6 waste carpet fluff), that contained 1.5% imine, was dissolved in 50 mL water and $CO_2$ was bubbled through the solution over 4 hours. The solution contained some resin-like, insoluble material. The water was removed under reduced pressure as before, and the brown crystalline residue was dissolved in 50 mL acetone. The resulting suspension was filtered through Celite® and the filtrate was concentrated in vacuo to provide brown crystals. These brown crystals were molten and after cooling, the crystalline residue (6.68 g) was analyzed by GC and was found to contain 87.67% caprolactam (±3.26) and 0.24% imine (±0.29).

EXAMPLE 3

Example 2 was repeated with crude caprolactam generated in Run 3.5 (nylon-6 waste carpet fluff). This sample contained 3% imine. The same procedure provided brown crystalline caprolactam that gave GC analysis of 85.97% caprolactam (±0.12) and imine 0.22% (±0.02).

EXAMPLE 4

A sample of 7.73 g caprolactam (Run 3.5—nylon-6 waste carpet fluff) was dissolved in 50 mL toluene and the mixture was refluxed until removal of the toluene-water azeotrope. A very small negligible quantity of water was removed. Then $CO_2$ was bubbled through the toluene solution for 4 hours, and some resin-like material was precipitated. The toluene was removed using a rotary evaporator with water bath temperature of 30° C., followed by evaporation under high vacuum. The residual brown, crystalline residue (6.46 g) was analyzed by GC and was found to contain 83.37% caprolactam (±3.19) and 1.05% imine (±0.07).

EXAMPLE 5

A sample of 7.08 g caprolactam (Run 3.5—nylon-6 waste carpet fluff) was dissolved in 50 mL acetone. As before, some resin-like material precipitated. Then $CO_2$ was bubbled through the mixture for 2.5 hours, and a white precipitate formed. The suspension was filtered through Celite® and the clear filtrate was concentrated in vacuo to provide 6.61 g of a brown crystalline solid that was analyzed by GC and found to contain 85.44% caprolactam (±2.95) and 1.06% imine (±0.15).

EXAMPLE 6

The procedure of example 5 was duplicated on a sample of 7.16 g caprolactam (Run 3.5—nylon-6 waste carpet fluff with 3 hours of $CO_2$ flow through the acetone solution. The same work-up (with Celite®) provided 7.002 g of a brown crystalline mass that was analyzed by GC and was found to contain 86.87% caprolactam (±1.18) and 0.92% imine.

EXAMPLE 7

A sample of 7.26 g caprolactam (Run 3.5—nylon-6 waste carpet fluff) was dissolved in 50 mL acetone, whereupon $CO_2$ was bubbled through the solution for 2.5 hours, and the resulting suspension was filtered through Silica gel (Merck, Rahway, N.J.) grade 60, 230–400 mesh, 60 Å). The filtrate was concentrated in vacuo and a brown, crystalline solid resulted (6.55 g). GC-analysis showed that the imine was completely removed from the crude pyrolyzate. It contained 91.71% caprolactam (±1.06) and no imine.

EXAMPLE 8

Run 3.3 was conducted in accordance with the teachings of U.S. Pat. No. 5,216,149, of common assignment with the present application, and said patent is incorporated herein by reference in its entirety as though the same were fully set forth herein. However, for convenience, this process is described briefly below.

The '149 patent teaches a feed stream of mixed plastics including nylon-6, and other materials such as polypropylene, is treated with a catalyst, which, is about 1–2 weight % KOH on $Al_2O_3$). The stream is heated to a desired temperature of about 250° to about 550° C., but more preferably about 300° to 450° C. In this case, heating occurred as follows: rate of about 40° C./minute to a temperature of about 293° C. and maintained at that temperature until a first set of pyrolysis products was collected and then further heated to about 397° C. until a second set of products was collected. The first set of products contained polypropylene and the second set of products contained caprolactam. These products were then passed through a hot electrostatic precipitator (ESP) of about 100° C., and then a cold ESP of about 40° C.

The pyrolyzate used in the present invention was generated in Run 3.3. Details of this run are set forth below. Run 3.3 was conducted in a fluidized bed reactor. Carpet fluff was fed continuously using a ram feeder. The temperature of this process was about 330–360° C., 801.6 g of fluff was fed during 310 minutes. The yield of the product recovered from nylon was 69.9%. 201 g of this product was collected in the hot ESP, and thereafter, 80 g was collected the cold ESP. This increased the yield to 83.8% for the hot ESP and 82.4% for the cold ESP.

EXAMPLE 9

Run 3.5 was conducted in a similar fashion, as follows: Run 3.5 was a continuous feed process taking place over 6 hours using 1022 g of carpet fluff. The reactor was heated to about 360° C. The catalyst used was 5% KOH on alumina. This run yielded a product containing 72% caprolactam 223 g of the product was collected in the hot ESP and contained 85.4% caprolactam. The cold ESP yielded 86.9% caprolactam from 131 g of product.

Although this invention has been described with respect to specific embodiments, it is to be understood that various modifications will become apparent to the skilled artisan in the field of nylon recycling, as such modifications when practiced will fall within the spirit and scope of the present invention.

I claim:

1. A method of removing 1,11-diamino-6-undecanone from the pyrolysis product of nylon comprising:

a) pyrolyzing nylon-6 to form a pyrolyzate containing a caprolactam mixture;
   b) dissolving the caprolactam mixture in a solvent to form a solution;
   c) passing carbon dioxide gas through the solution to form a precipitate;
   d) removing the precipitate from the solution; and
   e) recovering the purified caprolactam from the solution.

2. The method of claim 1 wherein the nylon is recycled.

3. The method of claim 1, wherein the solvent is selected from the group consisting of acetone, toluene and mixtures thereof.

4. The method of claim 1, wherein the solvent is acetone.

5. The method of claim 1, wherein the solvent is toluene.

6. The method of claim 1, wherein the source of nylon is carpet.

7. The method of claim 1, wherein the pyrolyzate containing a caprolactam mixture contains more than about 3% 1,11- diamino-6-undecanone.

8. The method of claim 1, wherein the purified caprolactam contains less than about 3% 1,11-diamino-6-undecanone.

9. The method of claim 1 which is carried out at ambient temperature.

10. The method of claim 1 further comprising the step of adding a catalyst to the pyrolyzate containing a caprolactam mixture.

11. The method of claim 10 wherein the catalyst is KOH on $Al_2O_3$.

12. The method of claim 10 wherein the amount of catalyst added is about 1–2% by weight.

13. The method of claim 10 wherein the amount of catalyst is about 5% KOH on alumina.

14. The method of claim 1 further comprising the step of recovering the solvent.

15. The method of claim 1 wherein the purified caprolactam is recovered from the solution by passing the solution through a filter material.

16. The method of claim 15 wherein the filter material is silica.

17. The method of claim 16 wherein the filter material is silica gel.

18. The method of claim 15 wherein the filter material is diatomaceous earth.

* * * * *